United States Patent
Wu

(10) Patent No.: US 8,825,137 B2
(45) Date of Patent: Sep. 2, 2014

(54) REPOSITIONABLE GYNECOLOGICAL APPLICATOR FOR IMAGE-GUIDED RADIOSURGERY (IGRS) AND IMAGE-GUIDED RADIATION THERAPY (IGRT) FOR LOCALIZED TREATMENT OF GYNECOLOGICAL TUMORS

(76) Inventor: Xiaodong Wu, Miami, FL (US)

( * ) Notice: Subject to any disclaimer, the term of this patent is extended or adjusted under 35 U.S.C. 154(b) by 898 days.

(21) Appl. No.: 12/045,000

(22) Filed: Mar. 9, 2008

(65) Prior Publication Data

US 2008/0219402 A1 Sep. 11, 2008

Related U.S. Application Data

(60) Provisional application No. 60/906,057, filed on Mar. 9, 2007.

(51) Int. Cl.
*A61B 5/05* (2006.01)
*A61B 6/04* (2006.01)
*A61N 5/10* (2006.01)

(52) U.S. Cl.
CPC ............. *A61B 6/0421* (2013.01); *A61N 5/1049* (2013.01); *A61N 5/1016* (2013.01)
USPC .............................. 600/426; 600/427; 378/65

(58) Field of Classification Search
USPC ......... 600/421, 423, 437, 442, 446, 453, 455, 600/459, 462, 463, 478, 429, 6, 2, 21, 407; 359/640; 378/95, 4; 73/584; 33/635
See application file for complete search history.

(56) References Cited

U.S. PATENT DOCUMENTS

| | | | | |
|---|---|---|---|---|
| 4,434,789 A * | 3/1984 | Kumar | | 600/6 |
| 4,804,270 A * | 2/1989 | Miller et al. | | 356/508 |
| 5,280,677 A * | 1/1994 | Kubo et al. | | 33/568 |
| 5,901,199 A * | 5/1999 | Murphy et al. | | 378/65 |
| 5,947,891 A * | 9/1999 | Morrison | | 600/6 |
| 6,641,518 B2 | 11/2003 | Wolfson et al. | | |
| 6,898,454 B2 | 5/2005 | Atalar et al. | | |
| 6,986,211 B2 * | 1/2006 | Gunderson | | 33/645 |
| 7,240,434 B2 * | 7/2007 | Lee et al. | | 33/1 M |
| 7,289,205 B2 | 10/2007 | Yaroslavsky et al. | | |
| 7,651,458 B2 * | 1/2010 | Mourtada et al. | | 600/6 |
| 2004/0133288 A1 * | 7/2004 | Hatcher et al. | | 700/56 |
| 2005/0197564 A1 | 9/2005 | Dempsey | | |
| 2006/0122493 A1 | 6/2006 | Atalar et al. | | |
| 2006/0235260 A1 * | 10/2006 | Mourtada et al. | | 600/7 |
| 2006/0241368 A1 * | 10/2006 | Fichtinger et al. | | 600/407 |
| 2006/0241432 A1 | 10/2006 | Herline et al. | | |
| 2007/0027352 A1 | 2/2007 | Mourtada et al. | | |
| 2007/0189455 A1 * | 8/2007 | Allison | | 378/95 |
| 2007/0196277 A1 | 8/2007 | Levin et al. | | |
| 2008/0030732 A1 | 2/2008 | Yaroslavsky et al. | | |

* cited by examiner

*Primary Examiner* — Unsu Jung
*Assistant Examiner* — Michael N Fisher
(74) *Attorney, Agent, or Firm* — Pinkert & Marsh, P.A.; Calrie Marsh, Esq.; Steven D. Pinkert, Esq.

(57) ABSTRACT

A method and apparatus for precisely reproducing the position of a vaginal cylinder in relation to a patient to ensure that a planned radiation dose can be delivered with high precision to the intended treatment target volumes. Treatment delivery is carried out by using an image-guided system to locate the position of the vaginal cylinder and comparing it to the coordinate of the vaginal cylinder obtained in the treatment plan. The displacement in the position of the vaginal cylinder from the treatment plan is corrected by calculating the transformation matrix and entering the resulting value into a position adjusting assembly which is attached to vaginal cylinder. The position adjusting assembly adjusts the vaginal cylinder to exactly reproduce its location relative to the patient's anatomy, eliminating geometric and dosimetric error.

5 Claims, 1 Drawing Sheet

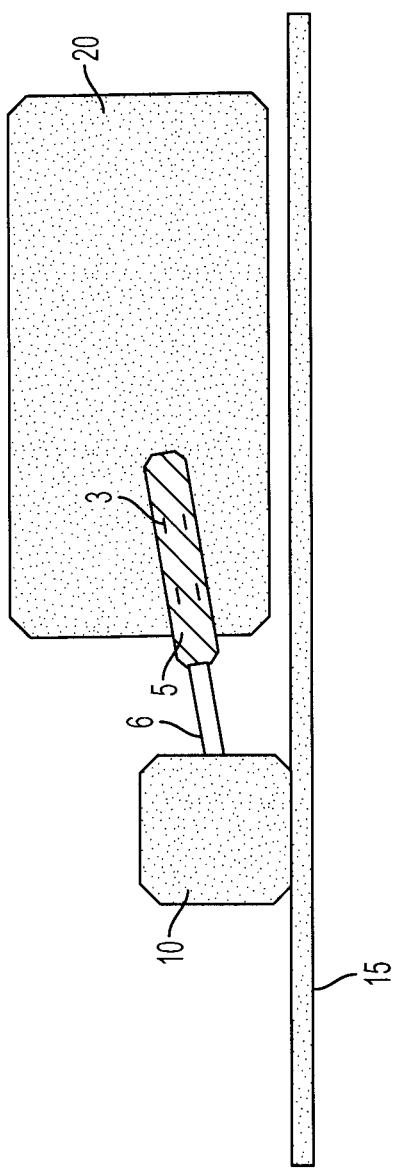

REPOSITIONABLE GYNECOLOGICAL APPLICATOR FOR IMAGE-GUIDED RADIOSURGERY (IGRS) AND IMAGE-GUIDED RADIATION THERAPY (IGRT) FOR LOCALIZED TREATMENT OF GYNECOLOGICAL TUMORS

CROSS-REFERENCE TO RELATED APPLICATIONS

This application claims the benefit of U.S. Provisional Application No. 60/906,057, filed Mar. 9, 2007. The entire disclosure of this prior application is hereby incorporated by reference.

STATEMENT REGARDING FEDERALLY SPONSORED RESEARCH OR DEVELOPMENT

This invention has been created without the sponsorship or funding of any federally sponsored research or development program.

FIELD OF THE INVENTION

The present invention relates generally to the high precision external beam radiation treatment of gynecological tumors to ensure minimal damage to the surrounding tissue.

BACKGROUND OF THE INVENTION

Brachytherapy (low dose rate or high dose rate) has been a common treatment modality for localized radiation treatment of gynecological tumors. Various types of applicators such as vaginal cylinders and tandem/ovoid applicator sets have been widely used. Stereotactic radiosurgery (SRS) has been recognized as an alternative to brachytherapy, since it also delivers conformal, localized radiation. The present invention deals with, but is not limited to, the radiosurgical treatment or conventional external beam radiation treatment of vaginal mucosa and surrounding tissue layers at risk.

In order to properly define the treatment volume, a vaginal cylinder with proper diameter is inserted into the patient's vagina. This approach is not uncommon for boost treatment(s) to the vaginal wall in conventional external beam radiation therapy. The challenge arises when higher fractional doses are used, and the vaginal cylinder position has to be reproducible with a high degree of precision for each treatment fraction.

Two potential errors need to be addressed: first, the incorrect cylinder position in relation to the radiation beams, and second, the inconsistent positional correlation between the cylinder and the patient's body. These two geometric errors will cause dosimetric errors. With the present invention both geometric error and dosimetric error can be reliably minimized.

SUMMARY OF THE INVENTION

The present invention provides a method and apparatus for minimizing the geometric error and dosimetric error associated with both conventional external beam radiation therapy and radiosurgical procedures used in treating gynecological tumors. The geometric error caused by incorrect cylinder position is minimized in this invention by utilizing an apparatus that allows adjustability and more exact placement of the vaginal cylinder. The principle of the present invention is to allow adjustability and therefore exact placement of the cylinder using quantified information from image guidance so that the inter-relational position between the cylinder and the patient's body can be precisely reproduced during each treatment fraction.

BRIEF DESCRIPTION OF THE DRAWING(S)

In describing the invention, reference will at times be made to the accompanying drawings in which:

FIG. 1 shows the apparatus of the invention, the repositionable gynecological applicator, as used in radiation therapy treatment.

DESCRIPTION OF THE INVENTION

Before the subject invention is described further, it is to be understood that the invention is not limited to the particular embodiments of the invention described below, as variations of the particular embodiments may be made and still fall within the scope of the invention. It is also to be understood that the terminology employed is for the purpose of describing particular embodiments, and is not intended to be limiting.

The details of one or more embodiments of the invention are set forth in the accompanying drawings and the description below. Other features, objects, and advantages of the invention will be apparent from the description and drawings, and from the claims. In the following description, numerous specific details are set forth to provide a thorough understanding of the embodiments. One skilled in the art to which this invention belongs will recognize, however, that the techniques described can be practiced without one or more of the specific details, or with other methods, components, materials, etc. In other instances, well known structures, materials or operations are not shown or described in detail to avoid obscuring certain aspects.

In this specification, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

FIG. 1 shows the apparatus of the invention, the repositionable gynecological applicator, which has two components: a vaginal cylinder 5 with embedded localization markers 3 (fiducials) and an extended portion or connector 6 without fiducials; and a position adjusting assembly 10. The vaginal cylinder 5 is made of durable plastic or other suitable material known to one skilled in the art; that allows for rigidity and keeps the vaginal cylinder 5 stationary during treatment. The position adjusting assembly 10 is attached to the vaginal cylinder 5 via the connector 6 and is utilized for adjusting the vaginal cylinder's position. The position adjusting assembly 10 is a mechanical setup suitable for purposes of adjusting the position of another device or mechanism with quantitative movement parameters (translational and rotational), not limited to a specific design, but is known to one skilled in the art to which it belongs. The position adjusting assembly 10 is firmly mounted to the treatment couch 15 at a reproducible position of the radiotherapy system. The position adjusting assembly 10 provides translational and rotational position adjustment to the vaginal cylinder 5.

In the preferred embodiment of the invention, the position adjusting assembly 10 is firmly mounted to the treatment couch and will be attached to the vaginal cylinder 5 via the connector 6 for adjusting the vaginal cylinder's 5 position.

The vaginal cylinder 5 with embedded fiducials 3 allows image-guided geometric reconstruction.

Using the Cyberknife™ as an example to describe the procedure and the methodology, the vaginal cylinder 5 is inserted into the patient's vagina 20 prior to computed tomography (CT) acquisition. The CT images are then acquired and used for treatment planning. The vaginal cylinder 5 is used to define the treatment volume. During treatment delivery, the orientations of both the patient 20 and the inserted vaginal cylinder 5 are obtained by the image-guided system. The patient 20 is first aligned to the treatment delivery system (global alignment) and the vaginal cylinder 5 is subsequently adjusted to the same position in relation to the patient 20 (local alignment), as was done during the original CT acquisition and the treatment planning.

During the treatment planning with CT images, the treatment alignment center is defined based on the patient anatomy, establishing the coordinate system which is denoted as $S_p$. The 3-D coordinates (both translational and rotational) of the vaginal cylinder 5, denoted as $C_{Sp}$, is then defined in the coordinate system, $S_p$.

During treatment setup, the image-guided system is used to adjust the patient's 20 orientation such that $S_p$ will be aligned with the delivery system's coordinate system, which is denoted as $S_T$. At this moment of alignment, the coordinates of the vaginal cylinder 5 in $S_T$ can be obtained through the image-guided system (using the cylinder itself or its imbedded fiducials) and is denoted as $C_{ST}$. The transformation matrix, denoted as A can be obtained by the following equation:

$$A = C_{Sp} C_{ST}^{-1}$$

In case the patient is not perfectly aligned with the SRS delivery system, the patient's coordinate system in $S_T$ can be identified as $S_p^T$, which represents the residual "misalignment" and the patient transformation matrix B can then be determined using the following equation:

$$B = S_T (S_p^T)^{-1},$$

and subsequently the transformation matrix A can obtained using the following equation:

$$A = C_{Sp} C_{ST}^{-1} B^{-1}.$$

Thus, the value of A obtained from either equation above provides the complete information needed to adjust the vaginal cylinder 5 to the same position in relation to the patient 20 and determine the treatment delivery position. The adjustment of the vaginal cylinder 5 is then carried out by the position adjusting assembly 10.

In the preferred embodiment, the position adjusting assembly 10 is mechanical with six adjusting knobs. Each knob is responsible for the quantitative adjustment of one degree of freedom (three translational and three rotational) of the vaginal cylinder 5 based on the quantitative information obtained from the resulting value of transformation matrix A. In other embodiments of the invention, the position adjustment assembly 10 can also be automated vis-à-vis certain motor-driven mechanisms known to one skilled in the arts to which this invention belongs. In other embodiments of the invention, the treatment delivery system will automatically align the vaginal cylinder 5 vis-à-vis the motor driven mechanisms The present invention can be used with any radiation therapy system with image-guidance features for delivering localized radiation doses to intra-cavitary disease sites, including but not limited to the vaginal wall or rectal wall.

It is to be understood, that the subject invention described herein is not limited to the particular embodiments of the invention described herein, as variations of the particular embodiments may be made and still fall within the scope of the invention as described herein. It is also to be understood that the terminology employed is for the purpose of describing particular embodiments, and is not intended to be limiting.

It should be noted that the methods and apparatus described herein are not limited to use only with the Cyberknife™ or other robotic radiosurgery treatment. The use of the Cyberknife™ within this patent application is meant as an example, and should not be construed in any way to limit the invention. In alternative embodiments, the methods and apparatus herein may be used in applications within other areas of the medical technology field as well as outside the medical technology field.

As various changes can be made in the above-described subject matter without departing from the scope and the spirit of the invention, it is intended that all subject matter contained in the above description, shown in the accompanying drawings, or defined in the appended claims will be interpreted as descriptive and illustrative, and not in a limiting sense. Many modifications and variations of the present invention are possible in light of the above teachings. It is therefore to be understood that within the scope of the appended claims, the invention may be practiced otherwise than as specifically described.

Equivalents

Those skilled in the art will recognize, or be able to ascertain using no more than routine experimentation, many equivalents to the specific embodiments of the invention described herein. Such equivalents are intended to be encompassed by the claims.

What is claimed is:

1. An apparatus comprising:
   a vaginal cylinder with embedded fiducials and a connector extension for insertion into a vagina;
   a position adjusting assembly consisting of six adjusting knobs, whereby each knob is responsible for the quantitative adjustment of one degree of freedom of the vaginal cylinder;
   the position adjusting assembly which is firmly mounted to a treatment couch of an image guided external beam radiation system connected to the vaginal cylinder via the connector extension to adjust a patient's position such that the treatment alignment center is aligned with the radiation delivery system's coordinate system;
   utilize a formula consisting of $A = C_{Sp} C_{ST}^{-1}$, where A is the transformation matrix, $C_{Sp}$ is the 3-D coordinates of the vaginal cylinder in a generated treatment dose plan and $C_{ST}$ is the coordinate of the vaginal cylinder for:
      comparing the current coordinate of the vaginal cylinder as reported by the image guidance system to the coordinate of the vaginal cylinder in the generated dose plan; and
      determining the difference or displacement of the vaginal cylinder by entering the correction value of each degree of freedom derived from the transformation matrix A into the position adjusting assembly to reproduce the location of the vaginal cylinder relative to the patient's anatomy, for the delivery of a radiation dose to the target volume based on the generated treatment dose plan.

2. The apparatus of claim 1 wherein the position adjusting assembly, which is firmly mounted to the treatment couch of the image guided external beam radiation system, provides six degrees of freedom for the quantitative adjustment of the vaginal cylinder.

3. The apparatus of claim 1 wherein the position adjusting assembly which is firmly mounted to the treatment couch of the image guided external beam radiation system is motorized for automated adjustment of the vaginal cylinder with a computer system of the image guided treatment delivery system.

4. The apparatus of claim 1 wherein the position adjusting assembly, which is firmly mounted to the treatment couch of the image guided external beam radiation system, is mechanical with six knobs, where each adjusting knob is responsible for the quantitative adjustment of one degree of freedom of the vaginal cylinder, three translational and three rotational.

5. A method for delivering gynecological image guided external beam radiosurgery or radiotherapy treatment including a method for planning gynecological image guided external beam radiotherapy treatment by bony landmark alignment comprising:
- attaching to a treatment couch of an image guided external beam radiation system an apparatus comprised of:
  - a vaginal cylinder with embedded fiducials for insertion into a vagina;
  - a position adjusting assembly, which is firmly mounted to the treatment couch of the image guided external beam radiation system and connected to the vaginal cylinder via a connector extension, to adjust a patient'position such that the treatment alignment center is aligned with the radiation delivery system's coordinate system;
- inserting the vaginal cylinder connected to the position adjusting assembly, which is firmly mounted to the treatment couch of the image guided external beam radiation system, into the vagina;
- using the position adjusting assembly to position the vaginal cylinder adjacent to a lesion;
- taking a CT of the patient which field includes the vaginal cylinder with surrounding tissue, the intended lesion and bony landmarks for setting alignment;
- importing CT data into a treatment planning system;
- defining a treatment target volume using the treatment planning system;
- defining a treatment alignment center using the treatment planning system; and
- generating a treatment dose plan; then
- recalling the generated treatment dose plan from an image guidance system;
- placing the patient on the treatment couch;
- inserting the vaginal cylinder connected to the position adjusting assembly, which is firmly mounted to the treatment table of the image guided external beam radiation system, into the vagina, in the same position as in the generated treatment dose plan;
- adjusting the patient position such that the treatment alignment center is aligned with the radiation delivery system's coordinate system;
- determining the position of the vaginal cylinder using an image guidance system;
- comparing the current coordinate of the vaginal cylinder as reported by the image guidance system to the coordinate of the vaginal cylinder in the generated treatment dose plan;
- determining the difference or displacement in the position of the vaginal cylinder using the formula $A=C_{Sp}C_{ST}^{-1}$, where A is the transformation matrix, $C_{Sp}$ is the 3-D coordinates of the vaginal cylinder in the generated treatment dose plan and $C_{ST}$ is the coordinate of the vaginal cylinder as reported by the image guidance system;
- entering the correction value of each degree of freedom derived from the transformation matrix A into the position adjusting assembly to exactly reproduce the location of the vaginal cylinder relative to the patient's anatomy; and
- delivering radiation dose to target volume.

* * * * *